United States Patent [19]
Voudouris

[11] Patent Number: 5,630,715
[45] Date of Patent: May 20, 1997

[54] ORTHODONTIC BRACKET WITH AN ENGAGEMENT MECHANISM FOR RETAINING AN ARCHWIRE

[76] Inventor: John C. Voudouris, 16 Doon Road, Willowdale, Ontario, Canada, M2L 1L9

[21] Appl. No.: 392,040

[22] Filed: Feb. 21, 1995

Related U.S. Application Data

[63] Continuation-in-part of Ser. No. 96,948, Jul. 23, 1993, abandoned, which is a continuation-in-part of Ser. No. 63,165, May 14, 1993, abandoned, which is a continuation-in-part of Ser. No. 7,095, Jan. 21, 1993, abandoned.

[51] Int. Cl.⁶ .................................................. A61C 3/00
[52] U.S. Cl. ........................................... 433/8; 433/13
[58] Field of Search .................................. 433/8, 9, 10, 11, 433/13, 14

[56] References Cited

U.S. PATENT DOCUMENTS

| | | | |
|---|---|---|---|
| 3,578,744 | 5/1971 | Wildman | 32/14 |
| 3,772,787 | 11/1973 | Hanson | 32/14 |
| 3,780,437 | 12/1973 | Wildman | 32/14 |
| 3,871,096 | 3/1975 | Wallshein | 32/14 |
| 4,023,274 | 5/1977 | Wallshein | 32/14 |
| 4,077,126 | 3/1978 | Pletcher | 32/14 |
| 4,144,642 | 3/1979 | Wallshein | 32/14 |
| 4,197,642 | 4/1980 | Wallshein | 433/11 |
| 4,248,588 | 2/1981 | Hanson | 433/11 |
| 4,386,909 | 6/1983 | Hanson | 433/20 |
| 4,419,078 | 12/1983 | Pletcher | 433/10 |
| 4,492,573 | 1/1985 | Hanson | 433/11 |
| 4,547,153 | 10/1985 | Taylor | 433/11 |
| 4,551,094 | 11/1985 | Kesling | 433/8 |
| 4,559,012 | 12/1985 | Pletcher | 433/10 |
| 4,561,844 | 12/1985 | Bates | 433/14 |
| 4,634,662 | 1/1987 | Rosenberg | 433/10 |
| 4,655,708 | 4/1987 | Fujita | 433/10 |
| 4,698,017 | 10/1987 | Hanson | 433/11 |
| 4,712,999 | 12/1987 | Rosenberg | 433/8 |
| 4,786,252 | 11/1988 | Fujita | 433/10 |
| 5,094,614 | 3/1992 | Wildman | 433/14 |
| 5,224,858 | 7/1993 | Hanson | |
| 5,322,435 | 6/1994 | Pletcher | |

*Primary Examiner*—Nicholas D. Lucchesi
*Attorney, Agent, or Firm*—Lloyd L. Zickert; Adam H. Masia

[57] ABSTRACT

A twin edgewise orthodontic bracket having an engagement mechanism for retaining an archwire, comprising a base having a pair of tie wing sets with an archwire slot and a slidable locking shutter or clip which in closed position retains the archwire in the archwire slot without the need for an elastic ligature and in open position allows placement and removal of the archwire.

44 Claims, 6 Drawing Sheets

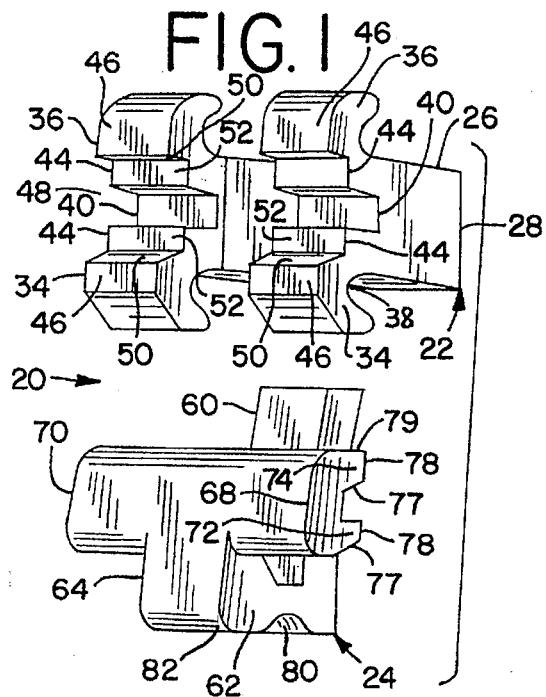
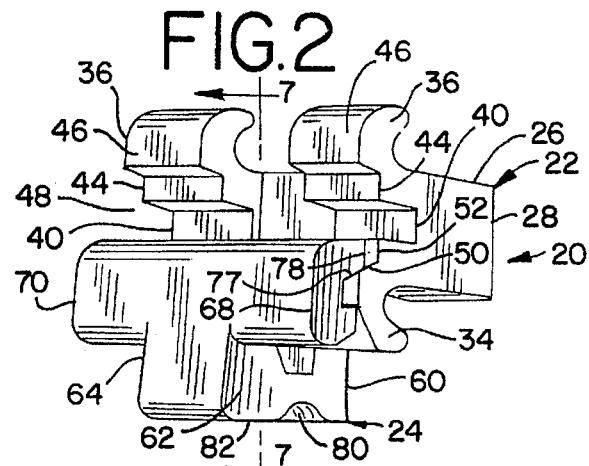
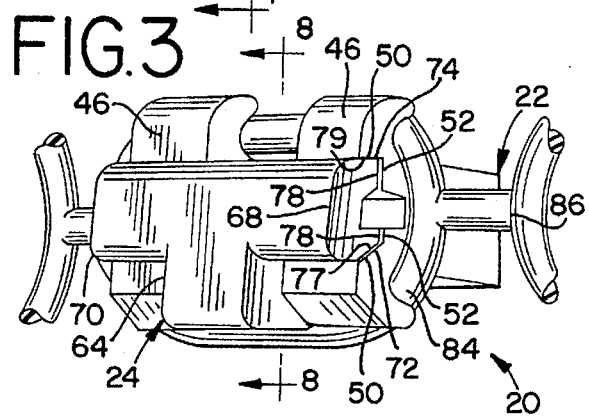
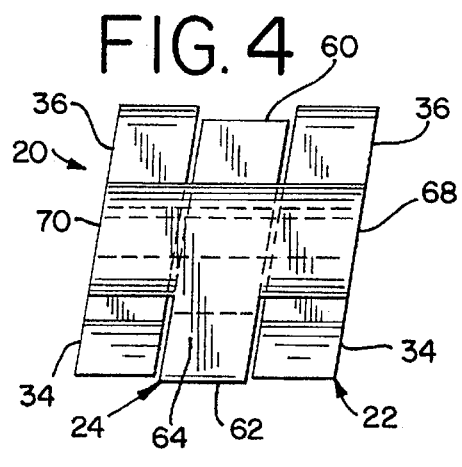
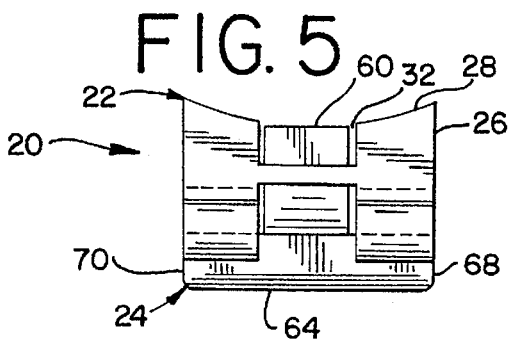
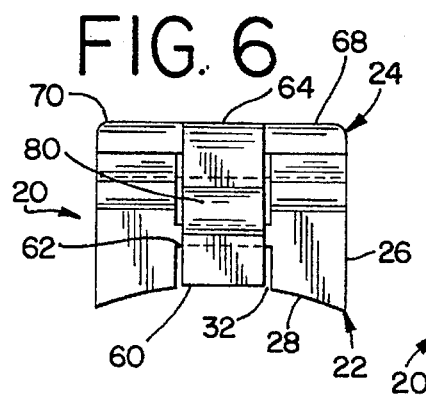
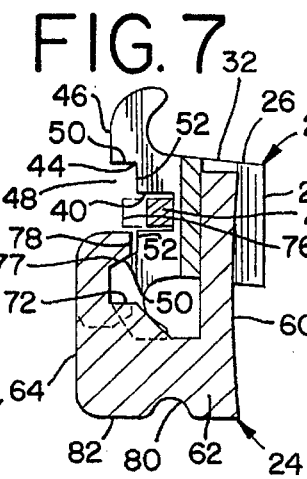
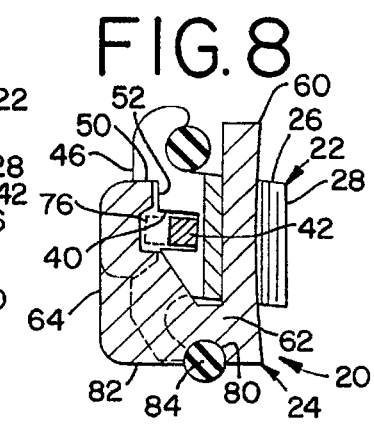

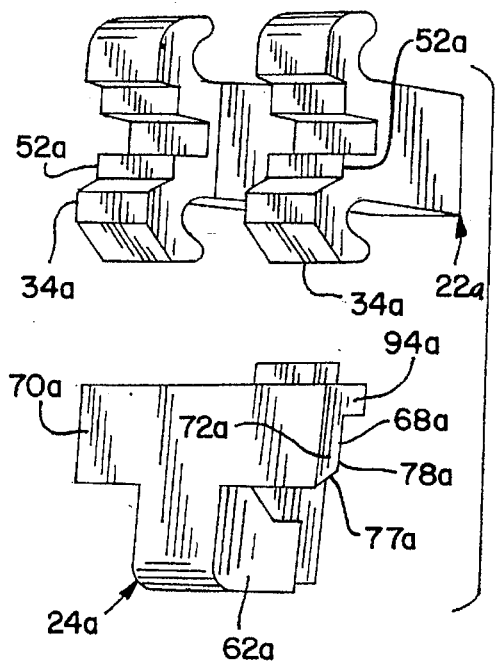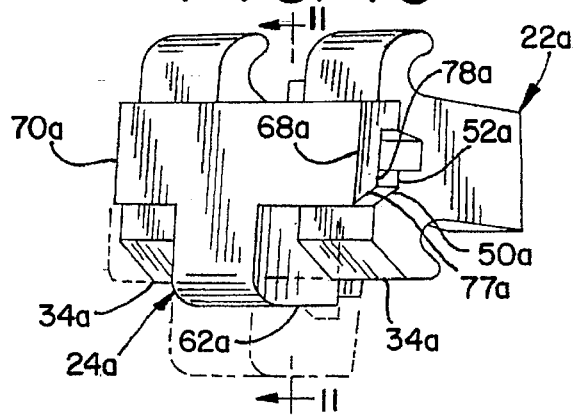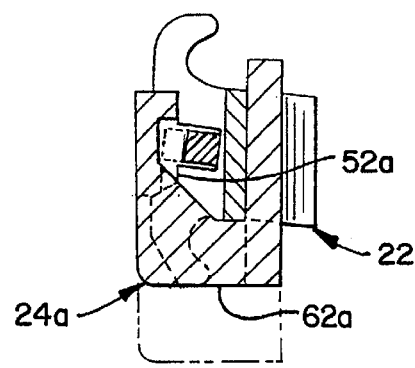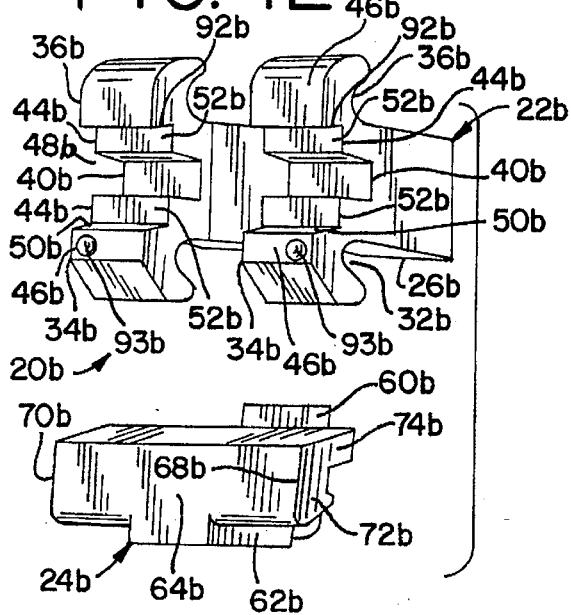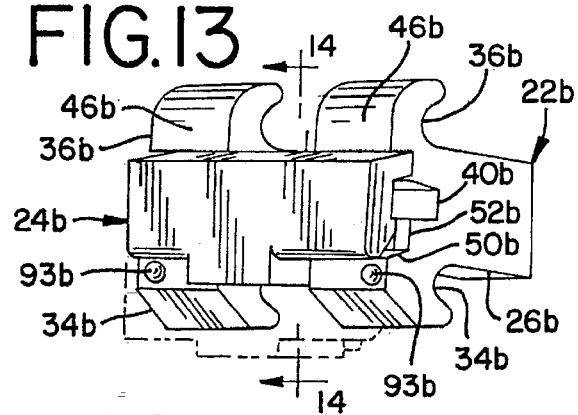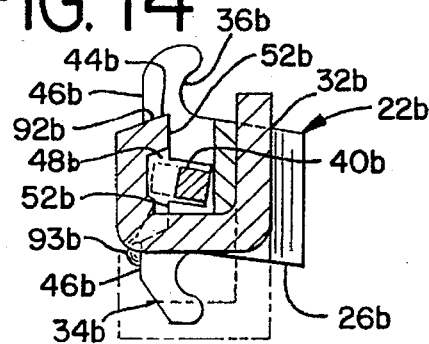

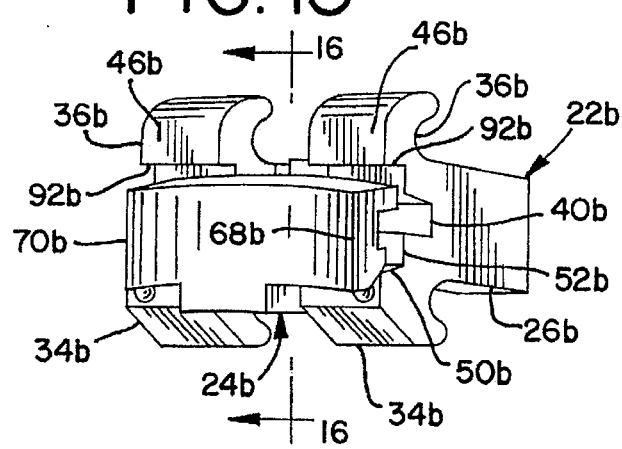
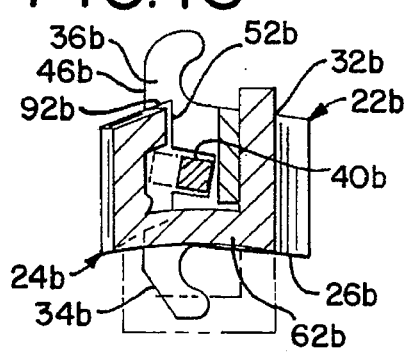
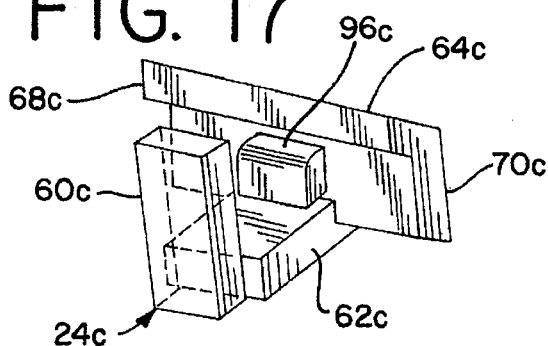
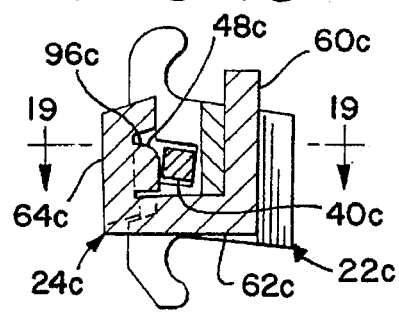
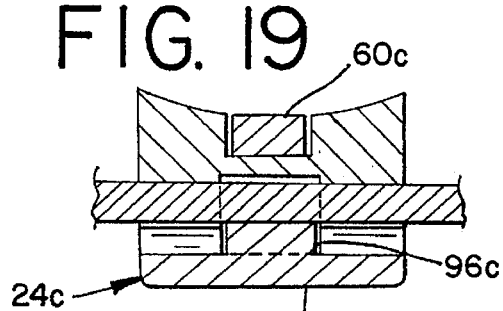
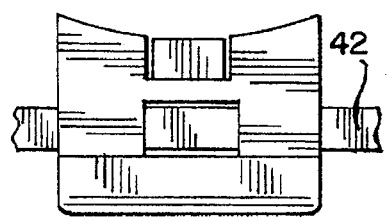
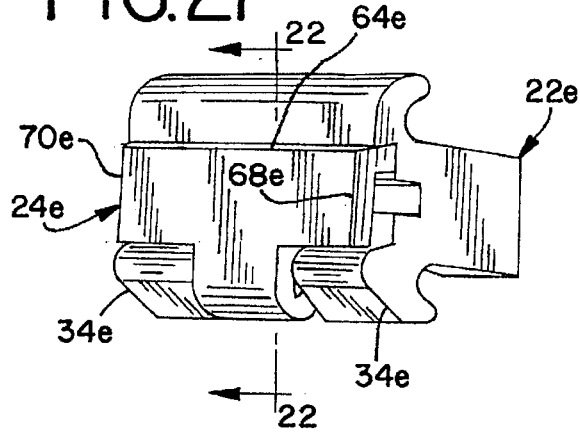
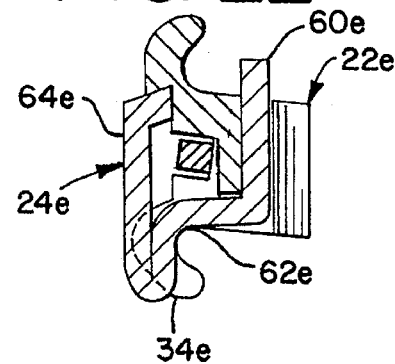

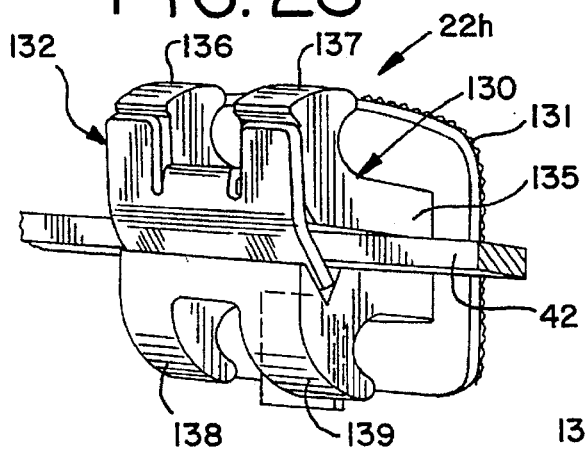
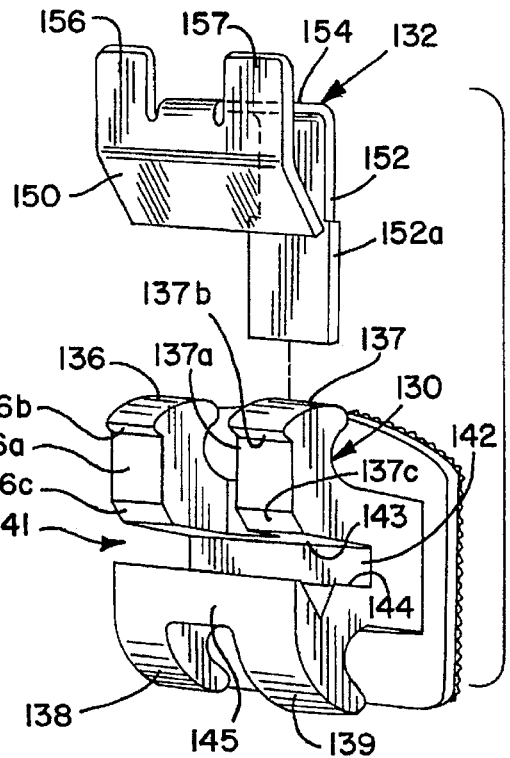
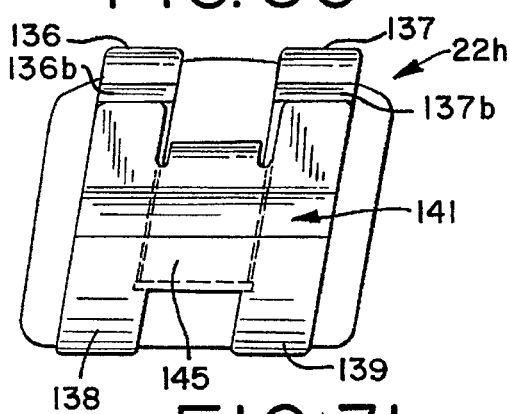
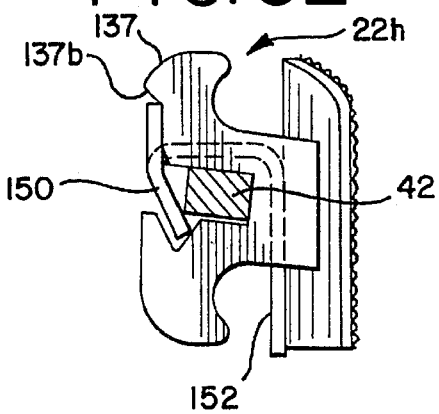
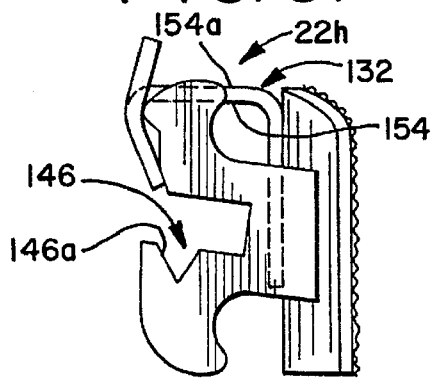
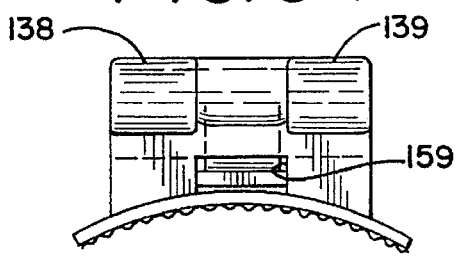

ORTHODONTIC BRACKET WITH AN ENGAGEMENT MECHANISM FOR RETAINING AN ARCHWIRE

DESCRIPTION

This application is a continuation-in-part application of my application Ser. No. 08/096,948, filed Jul. 23, 1993, now abandoned, which is a continuation-in-part application of my application Ser. No. 08/063,165, filed May 14, 1993, now abandoned, which is a continuation-in-part of my application Ser. No. 08/007,095, filed Jan. 21, 1993, now abandoned.

This invention relates in general to an edgewise orthodontic bracket having an engagement mechanism for retaining the archwire, and more particularly to a twin bracket having a locking shutter slidably mounted thereon between open and closed positions, whereby the locking shutter allows the placement and removal of an archwire from the bracket in the open position and prevents displacement of the archwire in the closed position without the need for an elastic or metal ligature.

BACKGROUND OF THE INVENTION

Heretofore, it has been well known that the edgewise orthodontic technique preferably requires an archwire to be attached to a tooth by securely placing the archwire in the mesial-distal archwire slot of a twin edgewise orthodontic bracket. The most common method for securing the archwire in the archwire slot has been by ligating an elastic ligature around the tie wings of the bracket and over the archwire at the mesial and distal sides of the bracket. While this method securely holds the archwire in place, it causes significant friction between the archwire and the bracket, thereby requiring greater forces to move teeth. Further, the ligatures need to be replaced quite often when they break, deteriorate, or when the archwire is changed. During treatment, the archwire may be changed many times. The process of constantly ligating each bracket with each change of the archwire greatly increases patient chair time. Additionally, elastic ligatures attract contaminating substances that increase the chances for the transmission of disease and decrease overall oral hygiene.

Due to these problems, numerous brackets have been created which include engagement mechanisms for retaining the archwire. For instance, U.S. Pat. Nos. 4,144,642; 4,248,588; 4,698,017; 3,772,787; 4,786,252; 4,559,012; 4,561,844; 4,655,708; 4,077,126; 4,419,078; 4,634,662 and 4,197,642 illustrate various designs for such brackets. However, while some of the bracket designs contemplate twin edgewise brackets, none have the structure, function, and reliability desired by the clinician.

SUMMARY OF THE INVENTION

The present invention provides an improved edgewise orthodontic bracket having an engagement mechanism for retaining the archwire, which decreases chair time by eliminating ligation time by only requiring a simple mechanical procedure. The improved bracket also decreases friction between the bracket and the archwire, and improves infection control and oral hygiene. The bracket of the present invention includes a twin edgewise bracket member having a base adapted to be attached to a tooth, and two sets of spaced apart occlusal and gingival tie wings extending buccal-labially from the base. The base also includes an occlusal-gingivally extending opening. Each set of tie wings define in their labial face a centrally located mesiodistally extending archwire slot segment, wherein the segments of the tie wing sets combine to define an archwire slot in the bracket member for receiving an archwire. In one embodiment each pair of occlusal and gingival tie wings also define in their labial face a mesial-distally extending deflecting recess for accommodating an archwire closure member, a locking shutter or clip. Further embodiments may include a mesial-distally extending locking recess in one of the occlusal or gingival tie wings of each set and a retaining member slot in the other tie wing of each set for coacting with an archwire closure member. A further embodiment includes locking tabs on the shutter engageable with locking ramps on the occlusal wings which prevent sliding of the shutter during push-out of the archwire.

The locking shutter is generally U-shaped and includes a guide bar or arm, an extension arm, and a locking body. The extension arm interconnects the guide bar and the locking body. The guide bar or arm is slidably received in an occlusal-gingival extending opening of the bracket member base, thereby guiding the movement of the locking shutter occlusal-gingivally. The locking body includes mesial and distal locking tabs aligned with the sets of tie wings to engage locking ramps during archwire push-out. Each tab is movable in the respective locking recess of each tie wing set when the locking shutter is moved between open and closed positions. In the closed position the locking shutter prevents the archwire from being displaced; while in the open position, the locking shutter allows placement of the archwire in the archwire slot and removal of the archwire from the slot.

It is therefore an object of the present invention to provide an improved self-engaging twin orthodontic bracket which allows easy placement and removal of the archwire and which prevents displacement of the archwire from the archwire slot during use in treating a patient.

A further object of the present invention is to provide an orthodontic bracket which significantly improves infection control and oral hygiene.

Another object of the present invention is to provide an orthodontic bracket with an archwire-engaging mechanism which allows the use of ligatures for additional rotational control.

Other objects, features and advantages of the invention will be apparent from the following detailed disclosure, taken in conjunction with the accompanying sheets of drawings, wherein like reference numerals refer to like parts.

DESCRIPTION OF THE DRAWINGS

FIG. 1 is an exploded perspective view of the orthodontic bracket of the present invention illustrating the twin bracket member or body and the locking shutter;

FIG. 2 is a perspective view of the bracket of FIG. 1 illustrating the locking shutter mounted on the bracket member in the open position;

FIG. 3 is a perspective view of the bracket illustrating the locking shutter mounted on the bracket member in the closed position and further illustrating one loop of a plastic chain attached to the bracket;

FIG. 4 is a front elevational view of the bracket of FIG. 1 illustrating the locking shutter mounted on the bracket member in the closed position;

FIG. 5 is a top plan view of the bracket of FIG. 1 illustrating the locking shutter mounted on the bracket member in the closed position;

FIG. 6 is a bottom plan view of the bracket of FIG. 1 illustrating the locking shutter mounted on the bracket member in the closed position;

FIG. 7 is a vertical sectional view of the bracket taken substantially along line 7—7 of FIG. 2, illustrating the locking shutter mounted on the bracket member in the open position and further showing a small archwire and a larger archwire in phantom within the archwire slot;

FIG. 8 is a vertical sectional view of the bracket taken substantially along line 8—8 of FIG. 3, illustrating the locking shutter mounted on the bracket member in closed position and further showing a small archwire and a larger archwire in phantom;

FIG. 9 is an exploded perspective view of a modified bracket of the present invention;

FIG. 10 is a perspective view of the modified bracket of FIG. 9 illustrating the modified locking shutter mounted on the bracket member in the closed position and further illustrating the modified locking shutter in the open position in phantom;

FIG. 11 is a vertical sectional view of the modified bracket of FIGS. 9 and 10 taken substantially along line 11—11 of FIG. 10 illustrating the modified locking shutter mounted on the bracket member in the closed position and further illustrating the modified locking shutter in the open position in phantom;

FIG. 12 in a exploded perspective view of another embodiment of the bracket of the present invention illustrating the bracket member and the locking shutter;

FIG. 13 is a perspective view of the bracket of FIG. 12 illustrating the locking shutter mounted on the bracket in the closed position and further illustrating the locking shutter in the open position in phantom;

FIG. 14 is a vertical sectional view of the bracket of FIGS. 12 and 13 taken substantially along line 14—14 of FIG. 13 illustrating the locking shutter mounted on the bracket in the closed position and the locking shutter in the open position in phantom;

FIG. 15 is a perspective view of the bracket of FIGS. 12 and 13 illustrating the flexing of the tabs on the locking shutter when the locking shutter is moved from closed to open positions;

FIG. 16 is a vertical sectional view of the bracket of FIGS. 12 and 13 taken substantially along line 16—16 of FIG. 15 illustrating the flexing of the extension arm of the locking shutter when the locking shutter is moved from closed to open positions and the locking shutter in the open position in phantom;

FIG. 17 is a rear perspective view of a further modified locking shutter illustrating a centrally disposed rotation wedge;

FIG. 18 is a vertical sectional view of the bracket of FIG. 17 like the sectional view of FIG. 14 and illustrating the modified locking shutter mounted on a bracket member in the closed position and engaging the archwire;

FIG. 19 is a detailed horizontal sectional view taken substantially along line 19—19 of FIG. 18 and illustrating the center rotation wedge;

FIG. 20 is a top plan view of a further modified bracket having a modified shutter and a full interconnector for the gingival tie wings as in a Mini-Tweed bracket;

FIG. 21 is a perspective view of the modified locking shutter for the bracket of FIG. 20 which includes an extension arm that opens the occlusal undercut;

FIG. 22 is a vertical sectional view of the bracket of FIG. 21 taken substantially along line 22—22 of FIG. 21;

FIG. 28 is a perspective view of a further embodiment of the invention showing the bracket attached to a mounting pad with the closure member in closed position for retaining an archwire;

FIG. 29 is an exploded perspective view of the bracket of FIG. 28 with the closure member separated from the bracket body;

FIG. 30 is a front elevational view of the embodiment of FIG. 28 with the closure member in open position;

FIG. 31 is a side elevational view of the embodiment of FIG. 28 with the closure member in open position;

FIG. 32 is a side elevational view of the embodiment of FIG. 28 with the closure member in closed position;

FIG. 33 is a top plan view of the embodiment of FIG. 28;

FIG. 34 is a bottom plan view of the embodiment of FIG. 28;

DESCRIPTION OF THE INVENTION

Figure 23:
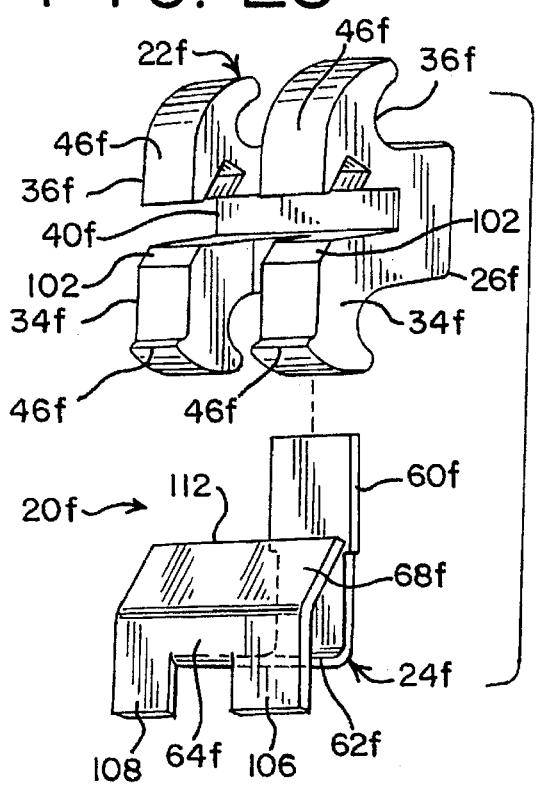
FIG. 23 is an exploded perspective view of a further modified bracket of the present invention.
Figure 24:
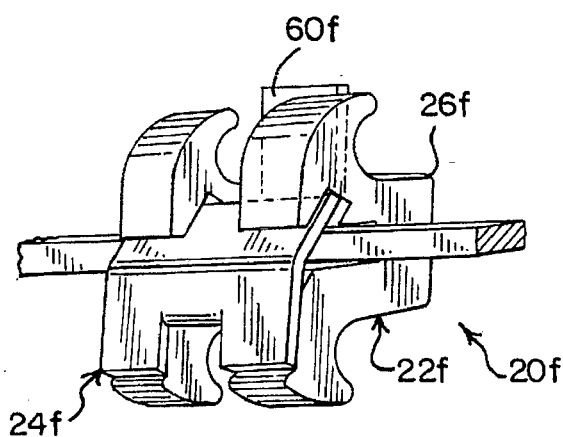
FIG. 24 is a perspective view of the modified bracket of FIG. 23 illustrating the locking shutter or closure in closed position with an archwire disposed within the archwire slot.

Referring now to the drawings, and particularly to the embodiment of FIGS. 1 to 8, the twin edgewise orthodontic bracket according to the present invention and generally designated by the numeral 20 includes a bracket member or body 22 and a locking shutter or clip 24 movable between open position for receiving an archwire and closed position for locking an archwire to the bracket. For illustrative purposes, the bracket member 22 shown is configured for a maxillary tooth, but it can be appreciated that the bracket 20 of the present invention could be used on a mandibular tooth. The bracket member 22 shown in FIGS. 1–8 also includes diagonal torque and diagonal angulation as described in U.S. Pat. No. 4,659,309 (which is incorporated herein by reference). However, the bracket of the present invention does not require that the bracket member have either of these features. Further, the torque and angulation values for any tooth would be in accordance with well known values of various systems.

The bracket member 22 includes a base 26 having a lingual tooth-attaching surface 28 adapted for direct attachment to a tooth or to a mounting pad that may be suitably attached to a tooth. For a metal bracket, the most common mounting pad or base would be the well known mesh pad. The base 26 includes an occlusal-gingivally extending opening 32 for guiding the movement of the locking shutter 24, as described below. Two spaced apart occlusal tie wings 34 and two spaced apart gingival tie wings 36 extend buccal-labially from the base 26. The combination of an occlusal tie wing 34 and a gingival tie wing 36 will be referred to hereinafter as a set of tie wings or a set of occlusal and gingival tie wings. The occlusal-gingival opening 32 in the base 26 is preferably centered between the two sets of tie wings although it should be appreciated that the opening may be offset if desired.

Each tie wing defines an undercut for receiving a ligature, and each set of tie wings includes a mesiodistally extending and labially opening archwire slot segment, and the segments collectively define the archwire slot 40 of the bracket for receiving an archwire 42.

A mesiodistally extending and labially opening notch or deflection recess 44 is provided in the labial surface 46 of each tie wing adjacent to the archwire slot segment. The combination of opposing notches 44 on each set of occlusal and gingival tie wings defines a locking recess 48, as best illustrated in FIG. 7. Each notch 44 on each of the four tie wings includes an upstanding wall 50 and a shoulder 52. The shoulders 52 on each set of tie wings are on the same level or plane. The upstanding wall 50 of the gingival tie wing 36 is substantially perpendicular to the shoulder 52 and the upstanding wall 50 of the occlusal tie wing 34 is preferably beveled or slanted toward the occlusal side of the bracket, thereby forming an obtuse angle with the shoulder 52, as illustrated in FIG. 7. It can be appreciated that the slope of the upstanding walls of the gingival tie wings may vary, as described below.

The locking shutter or clip 24 is generally mounted on the bracket and slidable between an open position, as shown in FIGS. 2 and 7, and a closed position, as shown in FIGS. 3 and 8. When the locking shutter 24 is in the open position, an archwire can be placed in or removed from the archwire slot 40. When the locking shutter 24 is in the closed position, the shutter prevents the archwire from being displaced from the archwire slot 40 while allowing limited labiolingual movement depending on archwire size. To prevent injury to the gingival tissue, the locking shutter is preferably mounted for movement on the occlusal side of the bracket member 22 which allows the orthodontist to operate or open the shutter away from the gingival area of the mouth when the bracket member 22 is secured to a maxillary or mandibular tooth.

The locking shutter 24 includes a guide bar or arm 60 which is slidably received in the occlusal-gingival opening 32 from the occlusal end. The movement of the locking shutter is controlled by the guide bar's occlusal-gingival movement in the opening 32. The guide bar 60 is integrally connected to an extension or connection arm 62 which extends labially therefrom between the sets of tie wings. The extension arm 62 generally fills the space between the two occlusal tie wings 34 while allowing flexibility in the locking shutter. The extension arm 62 is integrally connected to a locking body 64 which extends therefrom in substantially the same direction and substantially parallel to the guide bar 60. Accordingly, the guide bar 60 and the locking body 64 concurrently slide between open and closed positions.

The locking body 64 is structured to slide between the sets of tie wings when the locking shutter is moved between open and closed positions on the bracket member 22. A mesial locking tab 68 and a distal locking tab 70 respectively extend mesially and distally from the mesial and distal sides of the locking body 64 and are suited to engage the locking recesses 48 in the sets of occlusal and gingival tie wings. More specifically, each locking tab has a latching lip 72 and a stopping lip 74. These lips generally correspond to the upstanding walls 50 and the shoulders 52 of the opposing notches 44 which define the locking recesses, as described below.

When the locking shutter 24 is in the open position, the lower side 77 of the stopping lip 74 contacts the upstanding wall 50 of the occlusal tie wing 34, thereby maintaining the locking shutter 24 in open position and retaining the shutter on the bracket body, as illustrated in FIGS. 2 and 7. As illustrated in FIGS. 3 and 8, When the locking shutter 24 is in the closed position, the upper side 79 of the stopping lip 74 mates flush with the upstanding wall 50 of the gingival tie wing 36 and the end wall 78 mates flush with the shoulder 52 of the gingival tie wing 36, thereby preventing further gingival movement of the locking clip. As additionally illustrated in FIGS. 3 and 8, when the locking shutter 24 is in closed position, the lower side 77 of the latching lip 72 engages the upstanding wall 50 of the occlusal tie wing 34 and the end wall 78 engages flush with the shoulder 52 of the occlusal tie wing 34, thereby preventing the locking shutter from moving occlusally or being displaced from the locking recess. This construction allows the mesial and distal tabs extending from the locking body 64 to generally snap into the notches 44 of the locking recesses 48 when the locking shutter is moved to the closed position. Further, the lower side 77 of latching lip 72 is inclined to ramp over the occlusal tie wing 34 when opening the archwire slot. Likewise, the incline of the lower side 77 of the stopping lip 74 allows the stopping lip 74 to ramp over the archwire, if necessary, during movement to open position.

As the locking shutter moves between open and closed positions, the locking body 64 must be sufficiently flexible to allow the tabs 68 and 70, and specifically the latching lip 72, to deflect over the labial surface 46 of the occlusal tie wings 34. The locking body 64 is buccal-lingually flexible at its connection to the extension arm 62, and the locking tabs 68 and 70 are buccal-lingually flexible on the locking body 64 to allow buccolingual movement of the entire locking body. Thus, the locking shutter has a dual flexibility, as further described and illustrated below, which allows easy movement of the locking shutter between open and closed position and which reacts on the archwire to maintain the archwire in the archwire slot. The locking shutter of the present invention may be made of any suitable material, such as metal or plastic. It should also be appreciated that the locking shutter of the present invention could be made from multiple parts interconnected by any suitable means. The multiple parts could be of the same material or of different materials.

It should also be appreciated that to move the locking shutter from a closed position to an open position, the locking body and the locking tabs may be urged buccal-lingually and then occlusally by a suitable pliers instrument engaging the mesial and distal sides of the locking tabs or by engaging a scaler or the like at the gingival edge of the locking body and applying both labial and occlusal forces to drive the locking shutter to open position.

As shown in FIGS. 7 and 8, archwires of varying size may be used in the edgewise orthodontic treatment with the orthodontic bracket of the present invention. For instance, when a relatively small archwire 42 is used, the locking body and the locking tabs do not contact the archwire in the slot. This allows for some labial movement of the archwire, and it reduces the overall friction on the archwire while maintaining the archwire in the archwire slot. However, when a relatively larger archwire 76 is used, as shown in phantom in FIGS. 7 and 8, the locking body and the locking tabs allow considerably less labial movement, if any, of the archwire.

The orthodontic bracket of the present invention provides several advantages over elastic ligatures and other ligating methods in addition to decreasing the overall friction on the archwire. For instance, the locking shutter 24 further includes a mesial-distally extending and occlusally extending groove 80 in the occlusal surface 82 of the extension arm 62. This groove 80 allows for the placement of a loop 84 of a plastic chain or suitable strand member 86 on the bracket of the present invention to anchor the chain, as illustrated in FIGS. 3 and 8. An orthodontist, for example, may attach this type of plastic chain to facilitate movement of teeth along the same arch.

Another advantage of the present invention is that an additional elastic ligature may be placed over the entire orthodontic bracket 20 and the ligature retaining portions 38 of tie wings 34 and 36 when the locking shutter is in closed position to obtain additional rotational control. Hence, the locking shutter is constructed to leave the undercuts of the tie wings open.

Likewise, if the locking shutter 24 breaks or is removed by the orthodontist, the bracket member 22 may still be ligated in the usual manner by an elastic or metal ligature. This important advantage allows an orthodontist the option of providing additional rotational movement during treatment without the need to remove or replace the bracket member.

A modified locking shutter or clip 24a for mounting on an identical bracket member 22a is illustrated in FIGS. 9 to 11. The like parts of this bracket and other modifications are designated with the same legends and a corresponding suffix letter a. The modified locking shutter 24a differs from the locking shutter 24 in that the mesial and distal locking tabs 68a and 70a, respectively, do not include a latching lip. The extension arm 62a of locking shutter 24a is also modified in that it is illustrated without a groove for receiving a loop of a plastic chain, but it could have a groove if desired. When the locking shutter 24a is in the open position, only the edge or lower side of the stopping lip 94a engages or contacts the upstanding wall 50a of the occlusal tie wing 34a.

Another embodiment of the bracket of the present invention, generally indicated by numeral 20b, is illustrated in FIGS. 12 to 16. The like parts of this bracket are designated with the same legends and a corresponding suffix letter b. The bracket member 22b of this embodiment differs from bracket member 22 and generally includes a base 26b, an occlusal-gingival opening 32b in the base, two sets of occlusal and gingival tie wings 34b and 36b, and an archwire slot 40b in the labial surface 46b of the tie wings, all of similar construction to the bracket member 22. The bracket member 22b differs from bracket member 22 in that the mesiodistally extending and labially opening notch 44b in the gingival tie wing has an upstanding wall which is not perpendicular to the shoulder 52b. The upstanding wall of the gingival tie wing 36b, which will generally be referred to as the retaining wall 92b, is sloped or inclined and forms an acute angle with the shoulder 52b on the gingival tie wing 36b. Likewise, the upstanding wall 50b of the occlusal tie wing 34b is sloped or inclined and forms an obtuse angle with the shoulder 52b on the occlusal tie wing 34b similar to bracket member 22. The upstanding wall 50b and the retaining wall 92b are substantially parallel although it can be appreciated that they could be non-parallel. These upstanding walls and shoulders form the opposing notches 44b in the gingival and occlusal tie wings which form the locking recess 48b.

The locking shutter 24b illustrated in FIGS. 12 to 16 differs in that it includes a modified latching lip 72b. The locking shutter 24b generally includes a guide bar 60b, an extension arm 62b, and a locking body 64b having mesial and distal locking tabs 68b and 70b, respectively. Each locking tab has a latching lip 72b and a stopping lip 74b for engaging the notches 44b which define the locking recess 48b. When the locking shutter 24b is in the open position the stopping lip 74b mates with the upstanding wall 52b of the occlusal tie wing 34b, thereby maintaining the locking shutter 24b in open position and preventing separation of the locking shutter from the bracket body. When the locking shutter 24b is in the closed position, the stopping lip 74b mates with the retaining wall 92b and the shoulder 52b of the gingival tie wing 36b, and the latching lip 72b mates with the upstanding wall 50b and the shoulder 52b of the occlusal tie wing 34b, as illustrated in FIGS. 13 and 14. As the stopping lip 74b mates with the retaining wall 92b, the locking body is prevented from labial movement and thus prevents the archwire from being displaced. Further, it will be appreciated the gingival stopping lip serves to prevent the upward and outward escape or release of active archwires. On the other hand, where it is desired to move the locking shutter from the closed position to open position, the inclined upstanding wall 50b provides an angled surface for the labial and occlusal movement of the locking body. Thus, the tabs of the locking body 64b generally snap into the notches 44b of the locking recess 48b when the locking shutter is moved to the closed position and snap out of the locking recess when moved to the open position. The bracket member 22b also includes raised buttons 93b positioned on the labial surface 46b of the occlusal tie wings 34b. The gingival surface of these buttons 93b is generally a continuation of the upstanding wall 50b of the occlusal tie wing 34b and thus the button 93b and the upstanding wall 50b combine to form a lift ramp, as best seen in FIG. 14 in phantom. This lift ramp provides a surface for the latching lip 72b to slide buccallingually while the buttons 93b prevent unwanted displacement of the locking body from the closed position.

As further illustrated in FIGS. 15 and 16, the locking shutter has dual flexibility. The mesial and distal locking tabs 68b and 70b respectively are shown flexing or bending labially to allow displacement of the latching and stopping lips from the notches. The entire locking body also moves labially when the extension or connecting arm 62b, as shown in FIG. 16, bends or bows to allow displacement of the locking body from the closed position.

Another further modified locking shutter 24c, designed to snap into the locking recesses of bracket member 22c, is illustrated in FIGS. 17 to 19. The locking shutter 24c generally includes a guide bar 60c, an extension arm 62c, and a locking body 64c having mesial and distal locking tabs 68c and 70c, respectively. The locking shutter 24c further includes a centrally positioned rotation wedge 96c which extends the width of the locking body between the sets of tie wings, but does not extend the full width of the locking tabs 68c and 70c. As specifically illustrated in FIG. 18, this locking wedge intrudes between the sets of tie wings, thereby contacting along the archwire 42 to provide rotational control and hold the archwire against the bottom of the archwire slot. It should be appreciated that the cross section of the rotation wedge may be modified into various shapes without changing its function.

A modification of the bracket is illustrated in FIGS. 20 to 22 which differs from previous embodiments in that a modified shutter 24e as shown in FIGS. 21 and 22 is provided and the gingival wings have a full interconnector as in a Mini-Tweed bracket. The modified locking shutter 24e is structured to snap into the locking recesses of bracket member 22e, as illustrated in FIGS. 21 and 22. The locking shutter 24e generally includes a guide bar 60e, a modified extension arm 62e, and a modified locking body 64e having mesial and distal locking tabs 68e and 70e, respectively. The modified extension arm 62e extends labially from the guide bar 60e and then extends occlusally in a corresponding manner to the occlusal tie wings 34e. The modified locking body 64e extends gingivally from the extension arm 62e. This modification of the locking shutter still further opens the tie wing undercuts.

Still another embodiment of the bracket of the present invention is illustrated in FIGS. 23 to 26 and generally indicated by numeral 20f. The like parts of this bracket and other modifications are designated with the same legends and a corresponding suffix letter f. This bracket includes a bracket member 22f and a shutter or closure member 24f. The bracket member or body 22f of this embodiment is similar to bracket member 22 in that it generally includes a base 26f, an occlusal-gingival extending opening 32f in the base, two sets of occlusal and gingival tie wings 34f and 36f, and a mesial-distally extending archwire slot 40f in the labial surface 46f of the tie wings. Each set of tie wings includes a gingival tie wing 36f and an occlusal tie wing 34f.

Figure 25:
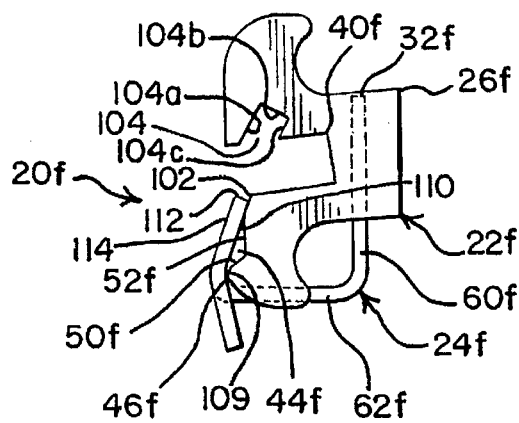
FIG. 25 is a side view of the modified bracket of FIG. 23 illustrating the locking shutter in open position.

The bracket member 22f differs from bracket 22 generally in the form of the locking recess. Each locking recess in bracket member 22f includes a mesiodistally extending and labially opening notch 44f in the occlusal tie wings 34f, as best illustrated in FIG. 25. The notch 44f has a shorter upstanding wall or ramp 50f which is sloped or inclined and forms an obtuse angle with a shoulder 52f which is occlusally-gingivally longer than and is disposed more labially than shoulder 52 of bracket 22. Notch 44f is therefore not as deep as notch 44, but is occlusally-gingivally longer than notch 44. Notch 44f also includes sloping face 102, which slopes gingivally and lingually toward the archwire slot 40f.

The bracket member or body 22f also differs from bracket 22 in that there is no mesiodistally extending notch on the labial faces of the gingival tie wings 36. The bracket body 22f includes a mesiodistally extending square deflecting recess slot 104 in each of the gingival tie wings adjacent the labial faces 46f. The slot 104 includes an angulated labial wall 104a disposed parallel to angulated lingual wall 104c, and a base wall 104b disposed at right angles to the labial wall 104a and the lingual wall 104c. The width of the slot between walls 104a and 104c may be greater than illustrated where the lingual wall 104c is disposed more lingual than shown particularly so the shutter 24f can extend lingually to engage a smaller wire. This retainer member or deflecting recess slot opens into the gingival wall of the arch wire slot 40f.

The locking shutter or closure member 24f illustrated in FIGS. 23 to 26 differs some from the like members of the other embodiments and includes a guide bar 60f, an extension arm 62f, and a locking body 64f having an integral closure member or flap 68f extending from the mesial and distal sides of the locking body 64f. The locking shutter is constructed of semi-rigid stainless steel having such a rigidity that it can withstand archwire forces without deforming. The locking body further includes mesial and distal latching wings or locking tabs 106 and 108 which extend occlusally from the locking body 64f and at an angle to the closure member 68f to define an indent 109. The locking body 64f, the closure member 68f, and the mesial and distal locking tabs 106 and 108 are integrally formed with the extension arm 62f, although other suitable connections between these parts may be utilized. The shutter or closure is generally semi-rigid, but the slits between the locking body and the locking tabs permit the closure to slide between open and closed positions.

When the locking shutter or closure member 24f is in the open position, as illustrated in FIG. 25, the lingual sides 110 of the mesial and distal locking tabs 106 and 108 engage the sloping faces 102 of the occlusal tie wings 34f and the indent 109 engages the labial cam surfaces or ramps 46f of the occlusal tie wings, thereby maintaining the locking shutter 24f in open position and preventing separation of the locking shutter from the bracket body 26f.

Figure 26:
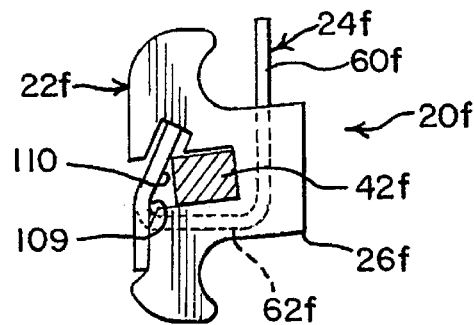
FIG. 26 is a side view of the modified bracket of FIG. 23 illustrating the locking shutter in closed position.

When the locking shutter 24f is in the closed position, as illustrated in FIG. 26, the closure member 68f extends into the deflection or deflecting recess slot 104 and is urged lingually by the overall construction of the closure to bear against the archwire as illustrated, such that the end wall 112 of the mesial and distal locking tabs engages the base wall 104b of the deflecting recess slot. The locking tabs are integrally connected by an intermediate portion, thereby enhancing the stiffness to withstand the archwire forces. Depending on the size of the archwire 42f and/or any push out force, the labial side 114 of the closure member may engage the labial wall 104a of the deflecting recess slot 104 or the lingual side 110 of the mesial and distal locking tabs can engage the lingual wall 104c of the deflecting recess slot. Preferably, the lingual wall 104c is disposed deep enough that the tabs will urge the archwire of whatever size against the bottom of the archwire slot without bottoming on the lingual wall 104c. When the labial side 114 mates with the labial wall 104a, the locking body is prevented from further labial movement and thus prevents the archwire from being displaced from the archwire slot. Thus, the locking shutter 64f coacts in a camming fashion with the deflection recess 44f to prevent the escape or release of active archwires by deflecting the shutter downward and cause the locking tabs to engage the ramps on the occlusal wings.

It should also be noted that in the closed position the mesial and distal locking tabs 106 and 108 respectively engage the mesial and distal shoulders or ramps 52f, thereby maintaining the locking shutter in closed position until sufficient force is applied by a clinician to open the closure member. During treatment, when the archwire forces are directed labially, the locking tabs dig in against the shoulders or ramps 52f, thereby further inhibiting possible sliding displacement of the closure. Further, the deflection slot 104 guards against such labial movement of the closure member that would allow the archwire to escape or become displaced from the archwire slot. Except when the archwire pushes out against the shutter, the end of the shutter is freely received in the deflection slot. Pushout forces cause the shutter to be deflected downwardly to activate the locking tabs against the ramps.

Figure 27:
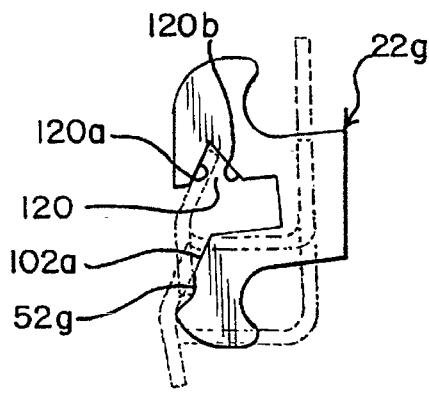
FIG. 27 is a side view of a still further modified bracket of the present invention illustrating the locking shutter or closure member in phantom and in both open and closed positions.
Figure 35:
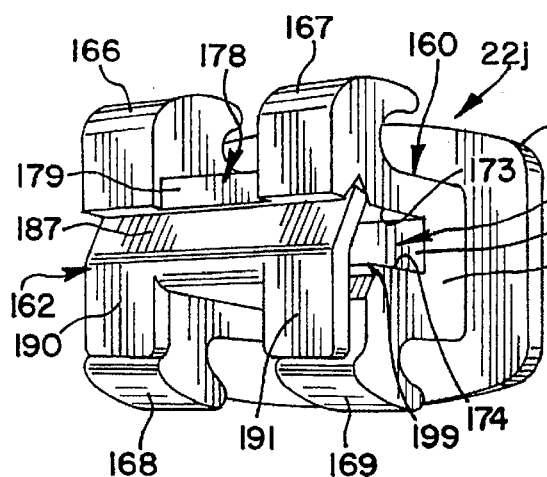
FIG. 35 is a perspective view of a still further embodiment of the invention.
Figure 36:
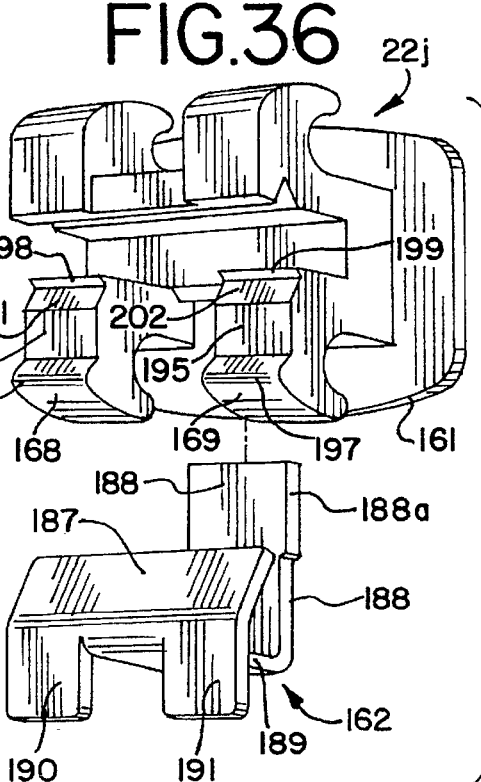
FIG. 36 is a view similar to FIG. 35 and illustrating the shutter displaced from the bracket.

A further modification of the bracket member is illustrated in FIG. 27. This bracket member is generally designated as 22g and differs from the bracket member 22f only in the shape of the deflection recess slot. The slot of this embodiment is designated by the numeral 120 and is of a triangular shape having a labial wall 120a and a lingual wall 120b. Further, the sloping member 102a is gingivally and lingually longer while the shoulder 52g is occlusally-gingivally shorter. Otherwise, the closure member is the same as that in the embodiment of FIGS. 23 to 26, and the operation is similar to the operation of the bracket 20f.

It should also be appreciated that while the bracket embodiments have been described whereby the closure member or shutter moves occlusally to open, these positions may be reversed for some teeth. Then, what was gingival will be occlusal, and what was occlusal will be gingival, and the closure member will move gingivally to open rather than occlusally. Otherwise, the operation of the bracket will be the same, although it is preferable that the closure member move occlusally to open. Further, should the shutter or closure become damaged and need to be removed or completely displaced from the bracket body, a standard ligature could be used as a back-up to ligate the archwire to the bracket body because of the tie wing undercuts, and the bracket can operate as a standard twin. This eliminates the need to debond and replace with a new bracket. Also, the tie wing undercuts facilitate the use of elastic chain.

The bracket embodiment of FIGS. 28 to 34, generally designated by the numeral 22h, differs from the embodiment of FIGS. 23 to 27 in that the occlusal tie wings are interconnected by a bar and the locking tabs are slightly narrower than the tie wings. This embodiment includes generally a bracket body 130 suitably attached to a mesh pad 131 and a shutter or archwire closure member 132. It will be appreciated that any of the previous embodiments could have the bracket body attached to a mounting pad which in turn facilitates the bonding of the bracket to a tooth. The mesh pad 131 is well known as being generally useful for bonding metal brackets to teeth, although it should be appreciated that the bracket body itself could be directly bonded to a tooth without the use of a pad if so desired.

The bracket body includes a base 135, upper or gingival tie wings 136 and 137, and lower or occlusal tie wings 138 and 139. The bracket of this embodiment is configured with angulation and torque of a chosen prescription for use on a left upper cuspid, although it will be appreciated that this version could be configured in any desired prescription for use on other upper or lower teeth. Each of the tie wings is provided with an undercut in the usual manner for purposes of facilitating the attachment of elastic chain or elastic ligatures. As particularly seen in FIG. 30, the upper and lower tie wings are parallel to each other and define a rhomboidal facial profile, thereby incorporating a desired angulation in the archwire slot. Any angulation may be incorporated in the bracket body depending on the prescription of the orthodontist and the tooth for which the bracket is designed. Moreover, the tie wings are of the same length so that the upper ends of the gingival tie wings 136 and 137 are coplanar and so that the lower edges of the occlusal tie wings are similarly coplanar and parallel to the upper edges of the gingival tie wings. Further, the mesial-distal edges of the bracket are likewise parallel to each other, thereby completing the rhomboidal profile as viewed from the labial.

Moreover, the bracket 22h, as viewed in FIG. 32, illustrates the torque in the archwire slot applicable for the system that is chosen and for the upper left cuspid tooth wherein the upper and lower sides of the archwire slot are parallel to the upper and lower sides of the bracket body such as to define a rhomboidal side profile. It will be appreciated that any suitable torque may be incorporated in the bracket body depending on the prescription of the brackets and the tooth for which the bracket is designed.

Essentially centered in the two sets of tie wings is a mesial-distally extending and labially opening archwire slot 141 having a bottom wall 142, an upper wall 143, and a lower wall 144. The upper and lower walls are parallel to each other and the bottom wall extends perpendicular to the upper and lower walls. The lower or occlusal tie wings 138 and 139 are interconnected by an interwing connecting bar 145. Thus, the labial faces of the tie wings 138 and 139 are coplanar with the labial face of the bar 145, or it may be considered that there is a continuous labial surface along and between the occlusal tie wings. Similarly, the bar 145 coacts with the occlusal tie wings such that the lower wall 144 of the archwire slot is continuous from the outer edge of one occlusal tie wing to the outer edge of the other tie wing. Adjacent the labial edge of the lower archwire slot wall 144 and extending mesial-distally across the tie wings 138 and 139 and the connecting bar 145 is a V-shaped deflection groove slot 146 which coacts with the closure member 132 as described below when the closure member is in closed position.

The closure member 132, also sometimes referred to as the shutter, coacts with the bracket body 130 to selectively open and close the archwire slot 141. The closure member includes an archwire slot closure panel or tab 150, a guide arm or bar 152, a connecting bar 154, and a pair of locking tabs 156 and 157. The guide bar 152 includes a slightly wider section 152a that matingly fits in an occlusogingivally extending opening 159 defined by the bracket body and the mesh pad so as to be slidable in the opening and guide gingival-occlusal movement of the closure member. The closure member is dimensioned so that when in closed position the slot closure panel or tab 150 closes over the open end of the archwire slot and the locking tabs 156 and 157 are received in recessed areas notches 136a and 137a on the labial faces of the gingival tie wings 136 and 137, as particularly seen in FIG. 32. At the upper ends of the recessed areas 136a and 137a, upwardly and outwardly inclined surfaces 136b and 137b coact with the recessed areas to define shoulders or ramps against which the upper ends of the locking tabs 156 and 157 of the closure member engage when the closure member is in closed position. Moreover, outward forces of the archwire tend to cause the gingival ends of the locking tabs to press in against the shoulders and thereby preclude sliding movement of the shutter or closure member. Beveled surfaces 136c and 137c are provided at the lower ends of recesses 136a and 137a to allow the occlusal end of the closure panel 150 to seat when the closure member is in open position in order to assist in retaining the closure member on the bracket body. The closure member 132 is preferably made of stainless steel of a thickness which can flex or give during the opening and closing operations at the connecting bar 154 and the tabs 156 and 157.

As shown in FIGS. 28 and 32 where the closure member 132 is in closed position, the labial end of the archwire slot is closed off to retain the archwire 42 in the archwire slot. Once the closure member is moved to open position as seen in FIG. 31, the archwire may be removed from the archwire slot or placed in the slot. When in closed position, a gingival force can be applied to the occlusal end 152b of the guide bar 152 to move the closure member to open position. During opening of the closure member, the gingival ends of the locking tabs are cammed labially by the inclined tie wing surfaces 136b and 137b and flexing occurs between the closure panel 150 and the guide bar 152 and between the locking tabs and the closure panel 150. In closed position the closure panel 150 is biased lingually to apply a force to the archwire to seat the archwire in the slot.

In order to assist in preventing the closure panel 150 from being forced labially by the archwire to the point that the archwire can release from the archwire slot, the occlusal end of the closure panel engages in the deflecting groove or slot 146, as seen in FIG. 32, and will engage against the wall 146a of the groove, thereby stopping the closure panel against further labial movement. Thus, not only does the springiness of the closure member serve to hold the archwire in the slot after it is suitably placed and the closure member is moved to closed position, but the deflecting groove 146 further assures that the closure panel of the closure member will not move labially beyond the groove in response to an archwire force to allow release of the archwire.

From the foregoing it is clear as to the operation of the embodiment of FIGS. 28 to 34 wherein an archwire may be placed in the bracket with the closure member 132 in open position, as shown in FIG. 31. Then, application of a force against the upper surface 154a of the connecting bar 154 will cause the closure member to slide to closed position, as shown in FIG. 32, thereby locking an archwire to the bracket. Thereafter when it is desired to open the bracket and move the closure member to an open position, a suitable force may be applied to the occlusal end 152b of the guide bar 152 to force the closure member gingivally to its open position so that the archwire may be removed.

It will be appreciated that the connecting bar 154 has a mesial-distal width such that it will easily move between the upper tie wings during the opening and closing operation of the closure member. Further, the locking tabs 157, while illustrated to be slightly mesial-distally narrower than the gingival tie wings, may be as wide as the upper tie wings if so desired. It will also be appreciated that the width of the locking tabs will in some respect dictate the springiness of the tabs wherein the narrower the width the more springy the locking tabs will be to facilitate moving the closure member to open position. Further, while the bracket 22h is configured so that the closure member moves gingivally to open and occlusally to close, it could be appreciated that the bracket and tie wings could be rotated 180 degrees whereby the closure member would move occlusally to open and gingivally to close.

The preferred embodiment of the invention is shown in FIGS. 35 to 39 and generally designated as 22j. This embodiment differs from the embodiment of FIGS. 28 to 34 in that it includes an interwing connecting bar between the gingival tie wings, a relatively wide-mouth V-shaped deflecting groove or slot in the gingival tie wings for receiving the gingival end of the closure panel of the shutter or closure member, a wedge-shaped stop on the occlusal tie wings to provide a resting area for the substantially flat gingival end of the shutter when it is in fully open position to prevent the shutter from inadvertently sliding into the archwire slot while the operator is attempting to place an archwire in the slot, a stop on the guide arm of the shutter for preventing the shutter from falling out of the opening and being completely disengaged from the bracket body during an opening procedure, and an inset for the interwing connecting bar to facilitate the use of auxiliaries such as a rotation wedge or ligature that passes through the interwing area.

This embodiment includes the bracket body 160 suitably attached to a mesh pad 161 and a shutter or archwire closure member 162. The mesh pad serves as bonding base to facilitate attachment of the bracket to a tooth, and the shape will be such as to mate with a tooth. The mesh pad is suitably connected to the bracket such as by welding. However, as previously mentioned, it should be appreciated that the bracket may also be directly attached or bonded to a tooth without the use of a pad.

The bracket body 160 includes a base 165, upper or gingival tie wings 166 and 167, and lower or occlusal tie wings 168 and 169. An archwire slot 172 is formed in the tie wings and extends mesial-distally and opens labially or buccally. The archwire slot includes upper and lower facing walls 173 and 174 and a bottom wall 175. The upper and lower walls are parallel to each other and the bottom wall extends generally perpendicular to the upper and lower walls. The upper wall may be considered the gingival wall, and the lower wall may be considered the occlusal wall.

It will be appreciated that the archwire slot will be configured to provide a suitable angulation and torque for a desired prescription as previously discussed.

Each of the tie wings is provided with an undercut or ligature receiving area to facilitate the attachment of elastic ligatures or an elastic chain as deemed desirable. Preferably, the upper and lower tie wings are parallel to each other, and together with the mesial and distal sides or edges of the bracket being parallel to each other, define a rhomboidal facial profile, thereby incorporating a desired angulation into the archwire slot in a similar manner to the embodiment set forth in FIGS. 28 to 34.

The upper or gingival tie wings are interconnected by an interwing connecting bar 178 to provide strength to the bracket. The connecting bar 178 includes a front face 179 that is inset from the front faces of the gingival tie wings 166 and 167 so that it can accommodate the mounting of auxiliaries such as a rotation wedge or ligatures. The connecting bar includes a top wall 180 that extends from the front wall 179 rearwardly or lingually to the base of the bracket. Extending mesial-distally along the undersides of the gingival tie wings 166 and 167 and the connecting bar 178 is a wide-mouth V-shaped deflecting groove or slot 182 defined by a forwardly and downwardly extending wall 183 and a rearwardly and downwardly extending wall 184. The deflecting groove serves to receive the upper free edge of the closure member as more particularly described below.

Figure 37:
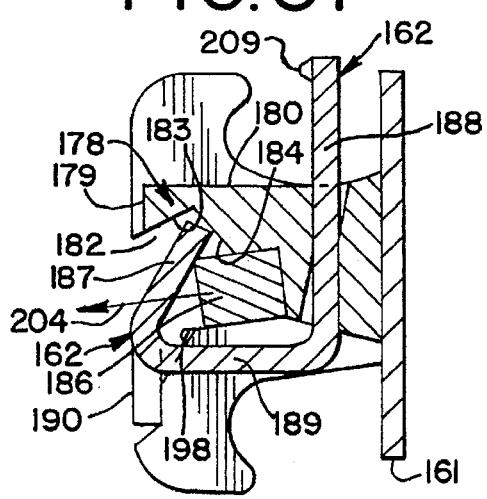
FIG. 37 is a sectional view taken through the center of the bracket showing the profile of the upper and lower tie wings and the relationship between the shutter and the bracket with the shutter in closed position retaining an archwire in the archwire slot.

The closure member or shutter 162 coacts with the bracket body 160 to selectively open and close the archwire slot 172 and respectively permit placement of an archwire or removal of an archwire such as the archwire 186 shown in FIG. 37. The shutter 162 includes an archwire slot closure panel 187, a vertical guide arm or bar 188, a connecting bar 189 extending between the closure panel 187 and the guide arm 188, and a pair of locking tabs 190 and 191. The connecting bar 189 extends generally labiolingually between the closure panel and the guide arm, and is substantially rectilinear in form. The guide arm 188 includes a slightly wider section 188a at the upper end for matingly fitting in an occlusogingivally extending opening or slot 193 formed in the bracket base 165. Accordingly, the guide arm is slidably received in the opening 193 to permit occlusogingival movement of the closure member. The opening 193 is flared or widened at the upper/gingival and lower/occlusal ends for purposes of facilitating the opening and closing of the shutter as more fully described below. It will be appreciated that the shutter is dimensioned so that when it is in closed position as shown in FIG. 37, the closure panel 187 closes over the open end of the archwire slot while the locking tabs 190 and 191 are respectively received in recesses 194 and 195 formed in the outer faces of the occlusal tie wings 168 and 169. The recesses define shoulders or ramps 196 and 197 on the respective occlusal tie wings 168 and 169. As seen particularly in FIG. 37, the thickness of the closure member material which includes the locking tabs is coordinated with the depth of the recesses in the occlusal tie wings so that the locking tabs are essentially flush with the labial surface of the bracket member, thereby accurately and complimentarily insetting the shutter into the bracket face.

Figure 39:
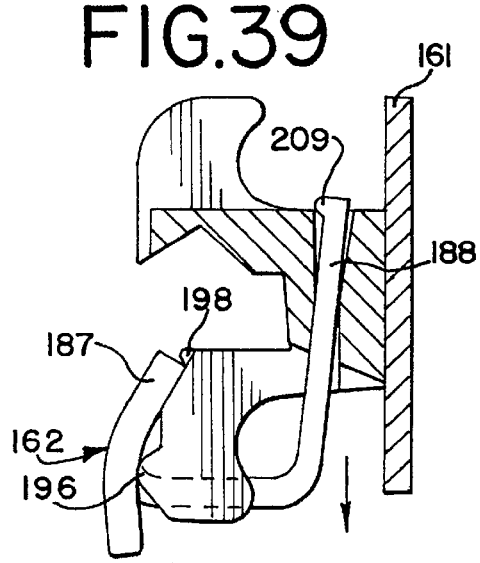
FIG. 39 is a view similar to FIG. 38 but illustrating the shutter in open position and maintaining that position by a wedge stop.

In order to define a resting position for the shutter when it is in open position, wedge-shaped stops 198 and 199 in the form of small, rounded facial extensions are formed on the occlusal tie wings adjacent the archwire slot. Further, inclined surfaces 201 and 202 are formed on the occlusal tie wings above the recesses 194 and 195 to coact with the wedge stops in defining a rest area for the substantially flat gingival end of the closure panel of the shutter when it is in open position, as illustrated in FIG. 39. The wedge-shaped stops prevent the shutter from moving inadvertently toward closed position and prevent the slot closure panel 187 from moving into the archwire slot during the time an archwire is being removed and/or being placed in the archwire slot.

When the shutter is in closed position, as seen in FIG. 37, an outward force or push-out of the archwire 186, as indicated by the arrow 204, will push the closure panel 187 outwardly so that the free edge or gingival-labial corner of the upper end engages the inclined surface 183 of the V-shaped groove 182 which causes a downward or occlusal camming of the shutter closure panel to force the locking tabs to dig in against the shoulders or ramps on the occlusal tie wings and thereby prevent sliding movement of the shutter toward open position. Thus, the free ends of the locking tabs 190 and 191 respectively engage against the ramps 196 and 197 to prevent the shutter from sliding occlusally and allowing the archwire to release itself from the archwire slot. It will be appreciated that the closure member or shutter is semi-rigid and preferably made of stainless steel in a suitable thickness, and the shutter can mildly spring under pressure as it would with a push-out of an archwire. The mild springiness would occur between the closure panel and the guide arm, and between the locking tabs and the closure panel.

During the opening of the shutter, a force is first applied to the upper end of the guide arm as illustrated by the force arrow 206 to drive the upper or gingival end of the arm lingually toward the bonding base and rock the shutter so that the locking tabs can be released and slide occlusally over the ramps on the occlusal tie wings. After applying the rearward pressure on the upper end of the arm, then a downward pressure may be substantially simultaneously applied to the gingival end of the guide arm, as indicated by the arrow 207, to drive the shutter to the open position, as shown in FIG. 39. The shutter will then take the position whereby the substantially flat gingival surface of the upper end of the closure panel 187 will abut against the wedge stops 198 of the lower or occlusal tie wings. The flaring of the opening 193 facilitates the rocking of the shutter when a force is applied at the upper end of the guide arm. Closing of the shutter is accomplished merely by applying an upward force against the bottom of the shutter such as in the area of the connecting bar 189. During opening and closing, the locking tabs, being on each side, stabilize the movement of the shutter in an occlusal-gingival path.

Figure 38:
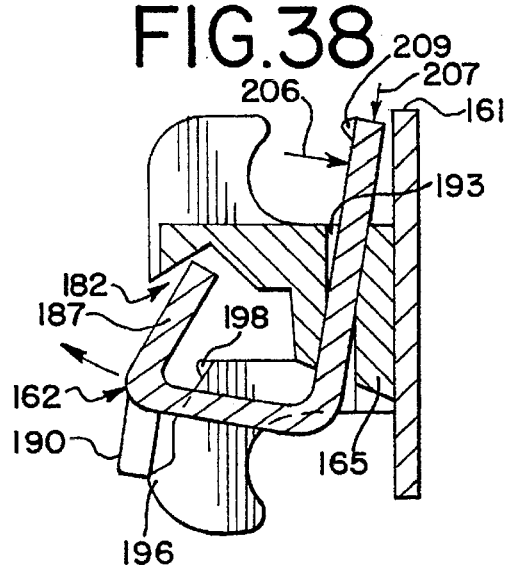
FIG. 38 is a view similar to FIG. 37 but illustrating the locking of the shutter relative to the bracket in the initial stage of opening the shutter.

In order to prevent inadvertent displacement of the shutter from the bracket when moving the shutter to the open position, a stop 209 is formed on the upper end of the guide arm 188, as particularly seen in FIGS. 38 and 39. Note that there is no stop on the shutter 162 illustrated in FIG. 36 prior to the assembly of the shutter with the bracket. After assembly is accomplished, a crimping stop can be formed in the guide arm at the end of the guide arm in order to thereafter prevent accidental removal of the shutter from the bracket body. During the opening cycle, the ends of the locking tabs are cammed over the ramps as the shutter is mildly flexed in order to permit spreading of the guide arm from the closure panel and the locking tabs and allowing the opening and closing action of the shutter. While the occlusal ends of the locking tabs are generally squared off, they could be knife-shaped if so desired and which may provide a better mating fit with the front face of the occlusal tie wings and the ramps.

Figure 40:
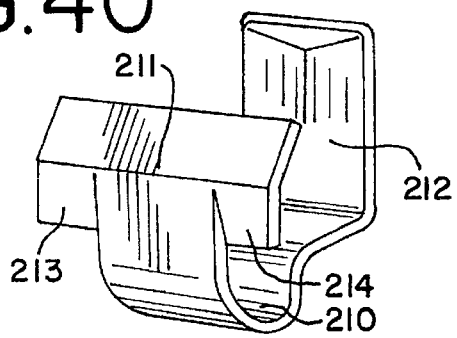
FIG. 40 is a perspective view of a modified shutter that may be employed in the bracket of FIG. 21.

A modification of the shutter is shown in FIG. 40 as applicable to a Mini-Tweed bracket, as shown in FIG. 21. This shutter is generally designated by the numeral 162k and includes an occlusal loop extension 210 for mesial-distally continuing the undercuts of the occlusal tie wings. Thus, the connecting bar in this embodiment which extends between the closure panel 211 and the guide arm 212 differs from that of the previous shutters in having a formation that generally matches the profile of occlusal tie wings. Further, the gingival wings may be joined together to present a flush surface across the upper part of the bracket, as shown in FIG. 21. With this modified shutter, the entire facial profile of the bracket will be essentially flush. It will be appreciated, however, that the shutter does also include locking tabs 213 and 214 which function in the same manner as the locking tabs of the previous embodiments.

All of the above embodiments and modifications of the self-ligating bracket invention may be coated with a metal-engaging or metal-bonding agent such as PTFE resin to provide a special lubricating coating which adheres to the metal surfaces. This special coating will inhibit calculus binding to the stainless steel surfaces of the present invention and facilitate archwire sliding in the archwire slot.

It will be understood that modifications and variations may be effected without departing from the scope of the novel concepts of the present invention, but it is understood that this application is to be limited only by the scope of the appended claims.

The invention is hereby claimed as follows:

1. A twin edgewise orthodontic bracket for attaching an archwire to a tooth comprising:

a bracket member including a base for attachment to the tooth, said base having an occlusal-gingivally extending opening, at least two sets of spaced apart occlusal and gingival tie wings extending from said base, each set of tie wings having a labial face which has a centrally disposed mesiodistally extending archwire slot segment, the segments of the tie wing sets combining to define an archwire slot of the bracket member for receiving the archwire, and said tie wings having a locking recess in the labial faces; and a slidable locking shutter movable between open and closed positions having a guide bar slidably received in said occlusal-gingival opening, a locking body for engaging said locking recess without covering the labial or lingual faces of the sets of occlusal and gingival tie wings when in closed position, and an extension arm connecting said guide bar to said locking body and movable between said sets of tie wings, wherein said locking shutter is slidably mounted on said bracket between open and closed positions, said locking body having means adapted to align with the sets of tie wings to close the archwire slot by engaging said locking recess, whereby the locking shutter allows placement and removal of the archwire when in the open position and prevents the displacement of the archwire from the bracket member when in the closed position.

2. The edgewise orthodontic bracket defined in claim 1, wherein said locking recess consists of opposing notches in said occlusal and gingival tie wings, each said notch having an upstanding portion and a shoulder portion.

3. The edgewise orthodontic bracket defined in claim 1, wherein the bracket member includes diagonal angulation and diagonal torque.

4. An edgewise orthodontic bracket for attaching an archwire to a tooth comprising:

a bracket member including a base for attachment to the tooth, said base having an occlusal-gingivally extending opening, at least two sets of spaced apart occlusal and gingival tie wings extending from said base, each set of tie wings having a labial face which has a centrally disposed mesiodistally extending archwire slot segment, the segments of the tie wing sets combining to define an archwire slot of the bracket member for receiving the archwire, and said tie wings having a locking recess in the labial faces, said locking recess consisting of opposing notches, each said notch having an upstanding portion and a shoulder portion, said shoulder portions being in a common plane and a slidable locking shutter having a guide bar slidably received in said occlusal-gingival opening, a locking body for engaging said locking recess, and an extension arm connecting said guide bar to said locking body and movable between said sets of tie wings, wherein said locking shutter is slidably mounted on said bracket between open and closed positions, said locking body having means adapted to align with the sets of tie wings to close the archwire slot by engaging said locking recess, whereby the locking shutter allows placement and removal of the archwire when in the open position and prevents the displacement of the archwire from the bracket member when in the closed position.

5. The edgewise orthodontic bracket defined in claim 4, wherein said upstanding portion of each gingival tie wing is perpendicular to said shoulder portion of each gingival tie wing and said upstanding portion of each occlusal tie wing forms an obtuse angle with each shoulder portion of each occlusal tie wing.

6. The edgewise orthodontic bracket defined in claim 4, wherein said upstanding portions on both gingival and occlusal tie wings are not perpendicular to said common plane of said shoulder portions.

7. The edgewise orthodontic bracket defined in claim 6, wherein said upstanding portion on each occlusal tie wing is part of a lift ramp for enhancing locking body movement between open and closed positions and the upstanding portion of each gingival tie wing prevents the locking body from moving gingivally and labially.

8. The edgewise orthodontic bracket defined in claim 7, wherein said lift ramps and said upstanding portions are positioned at approximately a twenty degree angle from said common plane of said shoulder portions.

9. The edgewise orthodontic bracket defined in claim 4, wherein said means further includes a latching lip and a stopping lip which extend lingually from said means and which are adapted to be received in said locking recess when said locking shutter is in a closed position.

10. An edgewise orthodontic bracket for attaching an archwire to a tooth comprising:

a bracket member including a base for attachment to the tooth, said base having an occlusal-gingivally extending opening, at least two sets of spaced apart occlusal and gingival tie wings extending from said base, each set of tie wings having a labial face which has a centrally disposed mesiodistally extending archwire slot segment, the segments of the tie wing sets combining to define an archwire slot of the bracket member for receiving the archwire, and said tie wings having a locking recess in the labial face; and a slidable locking shutter having a guide bar slidably received in said occlusal-gingival opening, a locking body for engaging said locking recess, and an extension arm connecting said guide bar to said locking body and movable between said sets of tie wings, wherein said locking shutter is slidably mounted on said bracket between open and closed positions, said locking body having means adapted to align with the sets of tie wings to close the archwire slot by engaging said locking recess, and wherein the locking body includes a rotation wedge which extends lingually between the sets of tie wings to engage the archwire, whereby the locking shutter allows placement and removal of the archwire when in the open position and prevents the displacement of the archwire from the bracket member when in the closed position.

11. An edgewise orthodontic bracket for attaching an archwire to a tooth comprising:

a bracket member including a base for attachment to the tooth, said base having an occlusal-gingivally extending opening, at least two sets of spaced apart occlusal and gingival tie wings extending from said base, each set of tie wings having a labial face which has a centrally disposed mesiodistally extending archwire slot segment, the segments of the tie wing sets combining to define an archwire slot of the bracket member for receiving the archwire, and said tie wings having a locking recess in the labial face; and a slidable locking shutter having a guide bar slidably received in said occlusal-gingival opening, a locking body for engaging said locking recess, and an extension arm connecting said guide bar to said locking body and movable between said sets of tie wings, wherein said locking shutter is slidably mounted on said bracket between open and closed positions, said locking body having means adapted to align with the sets of tie wings to close the archwire slot by engaging said locking recess, and wherein the extension arm defines a mesial-distally extending groove in its occlusal surface for receiving a strand member, whereby the locking shutter allows placement and removal of the archwire when in the open position and prevents the displacement of the archwire from the bracket member when in the closed position.

12. An edgewise orthodontic bracket for attaching an archwire to a tooth comprising:

a bracket member including a base adapted for attachment to the tooth, said base having an occlusal-gingivally extending opening, at least two sets of spaced apart gingival and occlusal tie wings extending from said base, each set of tie wings having a labial face which has a centrally disposed mesiodistally extending archwire slot segment, the segments of the tie wing sets combining to define an archwire slot of the bracket for receiving an archwire, and a locking recess in the labial face of said tie wings;

and a locking means slidably carried by the bracket member between open and closed positions for selectively locking an archwire in said archwire slot, said locking means including a guide means coacting with the occlusal-gingivally opening of the bracket member for guiding the movement of said locking means, an archwire engaging means connected to said guide means for coacting with each locking recess to selectively lock the archwire in the archwire slot without covering the labial or lingual faces of the sets of gingival and occlusal tie wings when in closed position, and said locking means being slidable between open and closed positions, whereby said locking means in the open position allows placement and removal of the archwire and in the closed position prevents the displacement of the archwire from the bracket member.

13. The orthodontic bracket defined in claim 12, wherein the archwire engaging means includes at least one locking tab extending into said locking recess when said locking means is in the closed position.

14. An twin orthodontic bracket for attaching an archwire to a tooth, said bracket comprising a base adapted to be secured to a tooth, two parallel spaced apart sets of tie wings extending from the base, each set including an occlusal and a gingival tie wing having labial surfaces and defining occlusal and gingival undercuts, an occlusal-gingival extending opening in said base, a mesiodistally extending and labially opening archwire slot in said tie wing sets, and means for retaining an archwire in the archwire slot movable between open and closed positions, said retaining means including a guide bar slidably received in said opening, tab means for selectively closing the labial opening of the archwire slot in both said tie wing sets, connecting means between the bar and tab means and means on the labial surfaces of said tie wings for lingually recessing the tab means on the tie wings when the retaining means is in closed position and for coacting with the tab means such as to prevent removal of said retaining means from the base and tie wings when the retaining means is in open position, and means on the tab means coacting with the archwire when the retaining means is in closed position to maintain the retaining means in closed position.

15. The twin orthodontic bracket as defined in claim 14, wherein said tab means includes tab means respectively aligned with the spaced apart tie wing sets.

16. The twin orthodontic bracket as defined in claim 15, wherein said tab means includes a lip adapted to overlie the archwire.

17. The twin orthodontic bracket as defined in claim 16, wherein said means on the labial surfaces of said tie wings includes notches on the labial surfaces of said occlusal and gingival tie wings adjacent to said slot.

18. The twin orthodontic bracket as defined in claim 17, wherein said notches extend mesiodistally.

19. The twin orthodontic bracket as defined in claim 14, wherein the connecting means is shaped to have an open occlusal undercut.

20. An edgewise orthodontic bracket for attaching an archwire to a tooth comprising:

a bracket member including a base for attachment to the tooth, said base having an occlusal-gingivally extending opening, at least two sets of spaced apart occlusal and gingival tie wings extending from said base, said tie wings having a labial face which has a centrally disposed mesiodistally extending archwire slot segment, the segments of the tie wing sets combining to define an archwire slot of the bracket member for receiving the archwire, and one of the occlusal or gingival tie wings of each set having a locking recess in the labial face, the other of the occlusal or gingival tie wings having a retainer member slot; and a slidable locking shutter coacting with the bracket member to selectively open and close the archwire slot for placing and locking an archwire in the slot and unlocking and removing the archwire from the slot, said shutter including a guide bar slidably received in said occlusal-gingival opening, a locking body for engaging said locking recess and said retainer member slots, and an extension arm connecting said guide bar to said locking body and movable between said sets of tie wings, wherein said locking shutter is slidably mounted on said bracket between open and closed positions, said locking body having latching wings adapted to align with and engage the locking recess of the tie wings for latching the shutter in closed position to close the archwire slot and means for closing the archwire slot and engaging in said retainer member slots, whereby the locking shutter allows placement and removal of the archwire when in the open position and prevents the displacement of the archwire from the bracket member when in the closed position.

21. The edgewise orthodontic bracket defined in claim 20, wherein said locking recess consists of a notch in said labial face of said tie wing, each said notch having an upstanding portion, a shoulder portion, and a sloping cam portion.

22. The edgewise orthodontic bracket defined in claim 21, wherein said upstanding portion of said tie wing forms an obtuse angle with said shoulder portion of said tie wing.

23. The edgewise orthodontic bracket defined in claim 20, wherein each said retainer member slot includes a lingual wall in spaced apart relation to a labial wall and said labial and lingual walls being connected by a base wall.

24. The edgewise orthodontic bracket defined in claim 23, wherein each said lingual wall is parallel to each labial wall and the base wall forms right angles with said labial and lingual walls.

25. The edgewise orthodontic bracket defined in claim 20, wherein each said retainer member slot includes converging lingual and labial walls.

26. The edgewise orthodontic bracket defined in claim 20, wherein a connecting bar is provided between the occlusal or gingival tie wings having the retainer member slot.

27. The edgewise orthodontic bracket defined in claim 26, wherein said retainer member slot is V-shaped.

28. The bracket of claim 27, wherein the tie wings include undercuts capable of receiving ligatures or elastic power chain.

29. An edgewise orthodontic bracket for attaching an archwire to a tooth comprising:

a bracket member including a base for attachment to the tooth, said base having an occlusal-gingivally extending opening, at least two sets of spaced apart occlusal and gingival tie wings extending from said base, each set of tie wings having a labial face which has a centrally disposed mesiodistally extending archwire slot segment, the segments of the tie wing sets combining to define an archwire slot of the bracket member for receiving the archwire, and one of the occlusal or gingival tie wings of each set having a notch in the labial face, the other of the occlusal or gingival tie wings having a deflection recess slot, wherein said deflection recess slots are rectangularly shaped; and a slidable locking shutter coacting with the bracket member to selectively open and close the archwire slot for placing and locking an archwire in the slot and unlocking and removing the archwire from the slot, said shutter including a guide bar slidably received in said occlusal-gingival opening, a locking body for engaging said notches and said deflection recess slots, and an extension arm connecting said guide bar to said locking body and movable between said sets of tie wings, wherein said locking shutter is slidably mounted on said bracket between open and closed positions, said locking body having latching wings adapted to align with and engage the notches of the tie wings for latching the shutter in closed position to close the archwire slot and tab means for closing the archwire slot and engaging in said deflection recess slots, whereby the locking shutter allows placement and removal of the archwire when in the open position and prevents the displacement of the archwire from the bracket member when in the closed position.

30. An edgewise orthodontic bracket for attaching an archwire to a tooth comprising:

a bracket member including a base for attachment to the tooth, said base having an occlusal-gingivally extending opening, at least two sets of spaced apart occlusal and gingival tie wings extending from said base, each set of tie wings having a labial face which has a centrally disposed mesiodistally extending archwire slot segment, the segments of the tie wing sets combining to define an archwire slot of the bracket member for receiving the archwire, and one of the occlusal or gingival tie wings of each set having a notch in the labial face, the other of the occlusal or gingival tie wings having a retainer member slot, wherein said retainer member slots are triangularly shaped; and a slidable locking shutter coacting with the bracket member to selectively open and close the archwire slot for placing and locking an archwire in the slot and unlocking and removing the archwire from the slot, said shutter including a guide bar slidably received in said occlusal-gingival opening, a locking body for engaging said notches and said retainer member slots, and an extension arm connecting said guide bar to said locking body and movable between said sets of tie wings, wherein said locking shutter is slidably mounted on said bracket between open and closed positions, said locking body having latching wings adapted to align with and engage the notches of the tie wings for latching the shutter in closed position to close the archwire slot and tab means for closing the archwire slot and engaging in said retainer member slots, whereby the locking shutter allows placement and removal of the archwire when in the open position and prevents the displacement of the archwire from the bracket member when in the closed position.

31. An edgewise orthodontic bracket for attaching an archwire to a tooth comprising:

a bracket member including a base adapted for attachment to the tooth, said base having an occlusal-gingivally extending opening, at least two sets of spaced apart gingival and occlusal tie wings extending from said base, each set of tie wings having a labial face which has a centrally disposed mesiodistally extending archwire slot segment, the segments of the tie wing sets combining to define an archwire slot of the bracket member for receiving an archwire, one of said gingival or occlusal tie wings of the sets having a deflection recess notch in the labial face of each tie wing, and the other of the occlusal or gingival tie wings of the sets having a retainer member slot;

and locking means slidably carried by the bracket member between open and closed positions for selectively locking an archwire in said archwire slot, said locking means including a guide means coacting with the occlusal gingival opening of the bracket member for guiding the sliding movement of said locking means, and an archwire engaging means connected to said guide means for coacting with said deflection recess notches and said retainer member slots of the tie wings to selectively lock the archwire in the archwire slot without covering the labial faces of the sets of occlusal and gingival tie wings when said locking means is in closed position, whereby said locking means in the open position allows placement and removal of the archwire and in the closed position prevents the displacement of the archwire from the bracket member.

32. An edgewise orthodontic bracket for attaching an archwire to a tooth comprising:

a bracket body having an archwire slot and an archwire slot closure movable between open and closed positions for selectively locking an archwire in said archwire slot, said bracket body including a base adapted for attachment to the tooth, an occlusogingival extending opening in the base, a pair of tie wing sets extending labially from the base, each set having a gingival and an occlusal tie wing, said archwire slot being disposed in the tie wings and extending mesiodistally and opening labially, one of the gingival or occlusal tie wings of each set having a deflection recess notch, and the other of said gingival or occlusal tie wings of each set having a closure recess slot, and said archwire slot closure including a generally U-shaped body having a guide portion slidably received in said opening, archwire slot closing tab means for covering the archwire slot at each set of tie wings when the closure is in closed position and means interconnecting the tab means to said guide portion, said tab means coacting with said closure recess slots when the closure is in closed position, and latching wings extending from said tab means for coacting with said tie wing deflection recess notches to latch the closure in closed position, and said latching wings and tab means formed to coact with means on the labial faces of said tie wings having the deflection recess notches to retain the closure on the bracket body when in open position.

33. An edgewise orthodontic bracket for attaching an archwire to a tooth comprising:

a bracket member including a base adapted for attachment to the tooth, said base having an occlusal-gingivally extending opening, at least two sets of spaced apart gingival and occlusal tie wings extending from said base, a connecting bar between one of the occlusal or gingival tie wings, said tie wings and connecting bar having a labial face which has a centrally disposed mesiodistally extending archwire slot for receiving an archwire, one of the gingival or occlusal tie wings of each set having a deflection recess notch in the labial face of each tie wing, and the other of the gingival or occlusal tie wings of each set having a retainer member slot or groove, and locking means slidably carried by the bracket member for selectively locking an archwire in said archwire slot, said locking means including a guide means coacting with the occlusal gingival opening of the bracket member for guiding the sliding movement of said locking means, an archwire engaging means connected to said guide means for coacting with said deflection recess notches and said retainer member slots of the tie wings to selectively lock the archwire in the archwire slot, and said locking means being slidable between open and closed positions, whereby said locking means in the open position allows placement and removal of the archwire and in the closed position prevents the displacement of the archwire from the bracket member.

34. The bracket of claim 33, wherein the connecting bar is between the gingival tie wings.

35. An edgewise orthodontic bracket for attaching an archwire to a tooth comprising:

a bracket member and a semi-rigid shutter member for ligating an archwire to the bracket member, said bracket member including a base for attachment to a tooth, said base having an occlusal-gingivally extending opening, two sets of spaced apart gingival and occlusal tie wings extending from the base and having undercuts for receiving auxiliaries or ligatures, a labially opening and mesial-distally extending archwire slot for receiving an archwire in said tie wings, a recess in the labial faces of said occlusal tie wings defining a shoulder or ramp, said archwire slot having opposed gingival and occlusal walls and a mesial-distally extending groove formed in the gingival walls of the gingival tie wings, said groove defined by a labial outwardly and downwardly extending wall and a lingual inwardly and downwardly extending wall, said shutter being slidably carried on said bracket member between open and closed positions for selectively locking an archwire in said archwire slot, said shutter having a guide arm slidably received in said opening, a closure panel sized to close the archwire slot, means connecting the closure panel to said guide arm, and locking tabs receivable in said recesses of said occlusal tie wings when the shutter is in closed position fitting substantially flush with the labial surface of the tie wings, said closure panel having a terminal edge receivable in said groove when the shutter is in closed position and the closure panel is forced labially by the archwire, whereby push-out of said archwire causes the closure panel to cam against the labial wall of said groove to force said closure panel downwardly and said locking tabs inwardly and downwardly against said ramps thereby preventing slidable movement of said shutter and escape of said archwire.

36. The bracket of claim 35, wherein the occlusal tie wings include a stop against which the terminal edge of the shutter closure panel rests when the shutter is in open position to prevent the shutter from entering the archwire slot area during placement of an archwire.

37. The bracket of claim 36, wherein a stop is provided on the free end of the guide arm to prevent the shutter from disengaging the bracket member during opening of the shutter.

38. The bracket of claim 37, wherein said base opening is flared at the gingival and occlusal ends to permit rocking of the shutter during the opening and closing of the shutter.

39. The bracket of claim 35, wherein the connecting bar between the guide arm and the closure panel extends substantially labial-lingually along a rectilinear path.

40. The bracket of claim 35, wherein the connecting bar between the guide arm and the closure panel is in the form of an occlusal loop that follows the contour of the occlusal tie wings.

41. The bracket of claim 35, wherein the interwing connecting bar includes a labial face that is inset from the labial surfaces of the gingival tie wings to accommodate the use of auxiliaries.

42. The bracket of claim 35, which further comprises an interwing connecting bar extending between one of the gingival or occlusal wings of said sets of wings.

43. The bracket of claim 42, wherein said interwing connecting bar extends between said gingival wings.

44. The bracket of claim 35, wherein said groove is V-shaped.

* * * * *